United States Patent [19]

Fox, Jr. et al.

[11] Patent Number: 4,535,078

[45] Date of Patent: Aug. 13, 1985

[54] ANTIBACTERIAL COMPOSITION COMPRISING SILVER SULFADIAZINE AND SODIUM PIPERACILLIN

[75] Inventors: Charles L. Fox, Jr., Fort Lauderdale, Fla.; Shanta M. Modak, River Edge, N.J.

[73] Assignee: The Trustees of Columbia University in the City of New York, New York, N.Y.

[21] Appl. No.: 597,531

[22] Filed: Apr. 6, 1984

[51] Int. Cl.³ .................. A61K 31/429; A61K 31/625
[52] U.S. Cl. .................................... 514/157; 514/253; 514/495
[58] Field of Search .............. 424/229, 250, DIG. 113

[56] References Cited

U.S. PATENT DOCUMENTS 4,112,090  9/1978  Saikawa et al. ..................... 424/251

OTHER PUBLICATIONS

"Piperacillin, a New Penicillin Active Against Many Bacteria Resistant to Other Penicillins", Fu et al., vol. 13, No. 3, Mar., 1978, Antimicrobial Agents and Chemotherapy, pp. 358–367.

Modak et al., "Control of Burn Wound Infections by Pefloxacin and its Silver Derivative", Burns, vol. 10, No. 3, pp. 170–178, (1983).

McManus et al., "Burn Wound Infection", The Journal of Trauma, vol. 21, No. 9, pp. 753–756, Sep. 1981.

Heggers et al., "Cerium Nitrate/Silver Sulphadiazine: Synergism or Antagonism as Determined by Minimum Inhibitory Concentration", Burns, vol. 5, No. 4, pp. 308–311, (1978).

Fox et al., "Virulence of Pseudomonas Infection in Burned Rats and Mice", Archives of Surgery, vol. 101, pp. 508–512, Oct. 1970.

Snelling et al., "Resistance of Gram–Negative Bacilli to Gentamicin", The Journal of Infectious Diseases, vol. 124, Supplement, pp. S264–S270, Dec. 1971.

Stone et al., "The Evolution and Spread of Gentamicin-Risistant Pseudomonads", The Journal of Trauma, vol. 11, No. 7, pp. 586–589, 1971.

Shulman et al., "Colonization with Gentamicin-Resistant Pseudomonas Aeruginosa, Pyocine Type 5, in a Burn Unit", The Journal of Infectious Diseases, vol. 124, Supplement, pp. S18–S23, Dec. 1971.

Chadwick, "Resistance of Pseudomonas Aeruginosa to Gentamicin", CMA Journal, vol. 109, pp. 585–587, Oct. 6, 1973.

Bryan et al., "Gentamicin Resistance in Pseudomonas Aeruginosa: R-Factor-Mediated Resistance", Antimicrob. Ag. Chemother., vol. 6, No. 2, pp. 191–199, Aug. 1974.

Fox, "Silver Sulfadiazine—A New Topical Therapy for Pseudomonas in Burns", Archives of Surgery, vol. 96, pp. 184–188, Feb. 1968.

Fox et al., "Control of Pseudomonas Infection in Burns by Silver Sulfadiazine", Surgery, Gynecology & Obstetrics; vol. 128, pp. 1021–1026, May, 1969.

Gayle et al., "Resistant Enterobacter Cloacae in a Burn Center: The Ineffectiveness of Silver Sulfadiazine", The Journal of Trauma, vol. 18, No. 4–5, pp. 317–323, May 1978.

Modak et al., "Silver Sulfadiazine (AgSD) Resistant Pseudomonas Infection in Experimental Burn Wounds", Estratto da Panminerva Medica Europa Medica, vol. 25, No. 3, pp. 181–188, (Jul.–Sep. 1983).

Modak et al., "Sulfadiazine Silver-Resistant Pseudomonas in Burns", Archives of Surgery, vol. 116, pp. 854–857, Jul. 1981.

Primary Examiner—Leonard Schenkman
Attorney, Agent, or Firm—Brumbaugh, Graves, Donohue & Raymond

[57] ABSTRACT

An antibacterial composition useful in burn therapy comprises silver sulfadiazine, sodium piperacillin and a physiologically acceptable carrier.

7 Claims, No Drawings

ANTIBACTERIAL COMPOSITION COMPRISING SILVER SULFADIAZINE AND SODIUM PIPERACILLIN

The present invention relates to an antibacterial composition useful in burn therapy.

BACKGROUND OF THE INVENTION

Topical therapy is now the first line of defense in the control of burn wound infection. From time to time the appearance of drug resistant organisms in burn wounds has impaired the efficacy of antimicrobial agents. Although silver sulfadiazine is the most effective agent to control burn wound infections, a few strains of Pseudomonas and other bacteria resistant to topical silver sulfadiazine have been reported in burn patients in the United States. In addition, silver sulfadiazine-resistant Pseudomonas infections have been observed in burn patients in other parts of the world.

SUMMARY OF THE INVENTION

It is, therefore, the object of the present invention to provide an antibacterial composition which is efficacious against silver sulfadiazine-resistant strains of Pseudomonas and other bacteria associated with burn wound infection.

In accordance with the present invention there is provided an antibacterial composition useful in burn therapy which comprises silver sulfadiazine, sodium piperacillin and a physiologically acceptable carrier. The composition contains a total of from about 35 millimoles to about 60 millimoles of silver sulfadiazine and sodium piperacillin per kilogram of the composition in a millimole ratio of silver sulfadiazine to sodium piperacillin of from about 2:1 to about 1:2. Preferably, the compositions contain about 30, 30; 30, 20; 30, 15; 15, 30; or 15, 20 millimoles of silver sulfadiazine and sodium piperacillin, respectively, per kilogram of the composition.

DETAILED DESCRIPTION OF THE INVENTION

As shown by the comparative in vitro and in vivo mice data set forth hereinafter, it was found quite unexpectedly that the antibacterial compositions of the present invention have greatly enhanced or synergistic activity against silver sulfadiazine-resistant strains of Pseudomonas and other bacteria associated with burn wound infection.

Silver sulfadiazine and sodium piperacillin are well known compounds, the latter compound being Compound No. 36 of the Saikawa et al. U.S. Pat. No. 4,112,090.

The compositions of the present invention can be prepared by mixing or blending the components thereof together. The silver sulfadiazine component can be prepared in situ by reacting equimolar amounts of silver nitrate and sodium sulfadiazine. Suitable physiologically acceptable carriers, such as a water-dispensible hydrophilic carrier or ointment, e.g., an oil-in-water dispersion, include, for example, those disclosed in the Fox U.S. Pat. Nos. 3,761,590, 4,049,802 and 4,404,197, the entire disclosures of which patents are hereby incorporated by reference herein. The compositions can be used by topically applying them in an effective antibacterial amount to the burn wound area in animal or man.

EXPERIMENTAL DETAILS

Materials

Sodium piperacillin (Pipracil) was supplied by Lederle Laboratories, Pearl River, N.Y.

Bacterial Strains

*Pseudomonas aeruginosa* (Boston) was the strain used in our previous investigations (Fox et al.; Arch. Surg. 101:508, 1970); *Ps. aeruginosa* (MNG-4) was isolated from a burned patient in Kasturba Medical College, Mangalore, India; *Ps. aeruginosa* (94-2) was from Burn Unit, Beverwijk, Holland.

In Vitro Assay of Microbial Inhibitions

Inhibition indices were obtained by tube dilution tests using nutrient broth. Growth in the presence and absence of drugs was observed by turbidity measurements after incubation at 37° C. for 24 to 48 hours (Fox et al.; Burns, 4:233, 1978).

Animal Experiments

Mice (female Swiss, 18 to 22 g) and rats (female Sprague Dawley, 180 to 200 g) were scalded using methods reported previously (Fox; Arch. Surg., 96:184, 1968; Fox et al.; Arch. Surg., 101:508, 1970). The wounds were contaminated one hour after burn with freshly prepared 18- to 20-hour broth culture of Pseudomonas diluted to optical density 0.30. Infection in mice was induced by immersing the tail in the culture, and in rats by swabbing 1 ml of the culture over the burn wound area.

The first treatment was administered four hours after infection by rubbing the medicated creams over all burned surfaces. All drugs used were mixed in the cream base used for 1% silver sulfadiazine. Thereafter, all animals were observed and treated once daily; the primary criterion was survival. Animals that died underwent autopsy and cultures were made of the cardiac blood to verify the presence of Pseudomonas. Rats were weighed, both before burn and on alternate days after burn.

Results

The comparative data in Table I show the greatly enhanced or synergistic activity of the combination of silver sulfadiazine and sodium piperacillin against a resistant strain of *Pseudomonas aeruginosa,* whereas such activity was not evident in combinations of silver sulfadiazine with a number of other antibacterial agents, namely, Furazin, Amikacin, Tobramycin, Chlorhexidine and Betadine.

The minimal inhibitory concentrations (MIC) of sodium piperacillin and various combinations with silver sulfadiazine against *Ps. aeruginosa* (Boston) are shown in Table II. The MIC of either silver sulfadiazine or sodium piperacillin are substantially higher than with mixtures of silver sulfadiazine and sodium piperacillin. The lowest concentrations of 6.0 nanomoles/ml of silver sulfadiazine and 7.5 nanomoles/ml of sodium piperacillin (total 13.5) which inhibited growth are considerably lower than the minimum inhibitory concentration (MIC) of silver sulfadiazine alone (50 n moles/ml) or sodium piperacillin alone (250 n moles/ml). Thus a true synergism exists.

The antibacterial spectrum of silver sulfadiazine and sodium piperacillin combinations are shown in Table III. These Tables II and III show clearly that when the combination is used, approximately 1/10 or 1/30 the amount of each is required for inhibition of the species tested.

Because wound exudates contain large amounts of protein and chloride, it is possible that some of the advantage of the combination might rest in the ability to resist a binding effect of the exudate constituents to the drugs. To evaluate this possibility, the antibacterial effect of the combination was studied in the presence of nutrient broth containing 10% human plasma; unlike silver sulfadiazine, no increase in MIC (reduced efficacy) was observed. (Table IV).

In vivo effectiveness of various topical agents

Our previous study showed that the in vivo drug resistance (in animal model) observd with some of the Pseudomonas stains occurs not only with silver sulfadiazine but also with tobramycin, gentamicin, mafenide acetate, chlorhexidine, silver nitrate, nitrofurazine and other metal sulfadiazines (Modak et al.; Arch. Surg., 116:854, 1981). Most of these agents were also not effective against a silver sulfadiazine-sensitive strain of *Pseudomonas aeruginosa* (Table I).

In marked contrast are the results using the combination silver sulfadiazine and sodium piperacillin against a sensitive strain of *Pseudomonas aeruginosa* (Boston) (Table V); and resistant strains of *Pseudomonas aeruginosa* (MNG 4) (Table VI) and *Pseudomonas aeruginosa* (942) (Table VII). This order of efficacy appeared with burned mice. With the sensitive Boston strain, silver sulfadiazine is effective, but when the concentration of silver sulfadiazine is reduced from 30 mM to 15 mM, the mortality increased significantly. At this level of silver sulfadiazine, addition of 20 mM of sodium piperacillin brought the mortality down appreciably. With the silver sulfadiazine resistant strains, the combination creates an effective topical therapy.

The results in burned rats are shown in Table VIII.

Previous studies show that when infection occurs in burned rats, there is a rapid fall of body weight as the animals deteriorate. Table IX shows the body weight of rats treated with the silver sulfadiazine/sodium piperacillin combination. Both the control and silver sulfadiazine group showed about 16% loss of body weight, while the silver sulfadiazine/sodium piperacillin group animals did not show any significant weight change.

The LD$_{50}$ of the combination of silver sulfadiazine and sodium piperacillin (1:1 molar solution) is 125 mg/kg, while individually silver sulfadiazine and sodium piperacillin showed an LD$_{50}$ of 160 mg/kg and 2000 mg/kg, respectively.

TABLE I

Topical Therapy of Burned Mice Infected with *Pseudomonas aeruginosa* Sensitive and Resistant to Silver Sulfadiazine

| TOPICAL AGENTS | % Mortality (8th Day Postburn) | |
|---|---|---|
| | Sensitive Strains | Resistant Strains |
| 30 mM Silver Sulfadiazine | 0 | 100 |
| 2% Nitrofurazine (Furazin) | 90 | 100 |
| Silver Sulfadiazine + Furazin(1:1) | 90 | 100 |
| 0.1% Amikacin | 80 | 80 |
| 0.1% Amikacin + 30 mM Silver Sulfadiazine | 75 | 80 |
| 1% Tobramycin | 100 | 100 |
| 1% Tobramycin + 1% Silver Sulfadiazine | 100 | 100 |
| 1% Chlorhexidine | 100 | 100 |
| 1% Chlorhexidine + 1% Silver Sulfadiazine | 100 | 100 |
| 1% Betadine | 100 | 100 |
| 1% Betadine + 1% Silver Sulfadiazine | 100 | 100 |
| 30 mM Sodium Piperacillin | 100 | 50 |
| 30 mM Sodium Piperacillin + 30 mM Silver Sulfadiazine | 0 | 0 |

TABLE II

Synergism of Silver Sulfadiazine and Sodium Piperacillin Against *Pseudomonas aeruginosa* (BOSTON)

| COMPOUNDS | Drug Concentration (nanomoles/ml) | | | | |
|---|---|---|---|---|---|
| AgSD* | 100 | 50 | 25 | 12.5 | 6.0 |
| Growth | 0 | 0 | + | + | + |
| PPR** | 500 | 250 | 125 | 60 | 30 |
| Growth | 0 | 0 | + | + | + |
| AgSD + | 12.5 | 12.5 | 12.5 | 12.5 | 12.5 |
| PPR | 60.0 | 30.0 | 15.0 | 7.5 | 3.75 |
| Growth | 0 | 0 | 0 | 0 | 0 |
| AgSD + | 6.0 | 6.0 | 6.0 | 6.0 | 6.0 |
| PPR | 60.0 | 30.0 | 15.0 | 7.5 | 1.0 |
| Growth | 0 | 0 | 0 | 0 | + |

*AgSD — Silver Sulfadiazine
**PPR — Sodium Piperacillin
Growth: 0 = no visible turbidity; + = visible turbidity

TABLE III

Antibacterial Spectrum of Silver Sulfadiazine and Sodium Piperacillin

| Organism | | Drug Concentration (nanomole/ml) | | | | | | | |
|---|---|---|---|---|---|---|---|---|---|
| *Staphylococcus* | AgSD* | 3 | 0 | 3 | 3 | 1.5 | 1.5 | .7 | .7 |
| *aureus* (47-1) | PPR** | 0 | 6 | 6 | 3 | 6 | 3 | 6 | 3 |
| | Growth | + | + | 0 | 0 | 0 | 0 | 0 | + |
| *Klebsiella* | AgSD | 3 | 0 | 3 | 3 | 1.5 | .7 | | |
| *Pneumoniae* | PPR | 0 | 6 | 6 | 3 | 3 | 3 | | |
| | Growth | + | + | 0 | 0 | 0 | 0 | | |
| *Eschericia* | AgSD | 0.7 | 0 | 0.7 | 0.7 | 0.7 | 0.7 | | |
| *coli* | PPR | 0 | 0.7 | 0.7 | 0.35 | 0.18 | 0.09 | | |
| | Growth | + | + | 0 | 0 | 0 | 0 | | |
| *Proteus* | AgSD | 1.5 | 0 | 1.5 | 1.5 | 1.5 | 0.7 | 0.7 | 0.7 |
| *vulgaris* | PPR | 0 | .35 | 0.35 | 0.18 | 0.09 | .35 | .18 | 0.09 |
| | Growth | + | + | 0 | 0 | 0 | 0 | 0 | 0 |

*AgSD — Silver Sulfadiazine
**PPR — Sodium Piperacillin
Growth: 0 = no visible turbidity; + = visible turbidity It should be noted that concentrations for each drug alone are not the inhibitory concentrations as in Table II, but rather they are the concentrations which in the combination were effective. These values are significantly lower than the inhibitory concentration for each drug alone.

TABLE IV

Effect of Plasma on the Synergistic Action to Silver Sulfadiazine and Sodium Piperacillin Against *Ps. Aeruginosa*

| | | Drug Concentration (nanomole/ml) | | | |
|---|---|---|---|---|---|
| Nutrient Broth | AgSD* + | 12.5 | 12.5 | 12.5 | 12.5 |

TABLE IV-continued
Effect of Plasma on the Synergistic Action to Silver Sulfadiazine and Sodium Piperacillin Against *Ps. Aeruginosa*

| | | Drug Concentration (nanomole/ml) | | | |
|---|---|---|---|---|---|
| | | 60.0 | 30.0 | 15.0 | 7.5 |
| | PPR** | | | | |
| | Growth | 0 | 0 | 0 | 0 |
| Nutrient Broth containing 10% plasma | AgSD + PPR | 12.5 60.0 | 12.5 30.0 | 12.5 15.0 | 12.5 7.5 |
| | Growth | 0 | 0 | 0 | 0 |

*AgSD — Silver Sulfadiazine
**PPR — Sodium Piperacillin
Growth: 0 = no visible turbidity; + = visible turbidity

TABLE V
Topical Therapy of Burned Mice Infected with *Pseudomonas aeruginosa* (BOSTON) - Sensitive

| | No. of Mice | % Mortality - Days Post Burn | | | |
|---|---|---|---|---|---|
| | | 2 | 4 | 6 | 8 |
| CONTROL | 25 | 28 | 80 | 92 | 100 |
| AgSD (Alone)* | | | | | |
| 30 mM | 25 | 4 | 4 | 8 | 12 |
| 15 mM | 25 | 0 | 16 | 28 | 40 |
| PPR (Alone)** | | | | | |
| 30 mM | 25 | 0 | 28 | 40 | 80 |
| 20 mM | 25 | 0 | 72 | 100 | 100 |
| AgSD + PPR (Combination) | | | | | |
| 30 mM AgSD + 30 mM PPR | 25 | 0 | 0 | 0 | 0 |
| 30 mM AgSD + 20 mM PPR | 25 | 0 | 0 | 0 | 0 |
| 15 mM AgSD + 20 mM PPR | 25 | 0 | 0 | 0 | 12 |

Drug concentration is mM per Kg of ointment used in therapy.
*AgSD — Silver Sulfadiazine
**PPR — Sodium Piperacillin
This table is the summary of two or three experiments.

TABLE VI
Topical Therapy of Burned Mice Infected with *Pseudomonas aeruginosa* (MNG-4) - Resistant

| | No. of Mice | % Mortality - Days Post Burn | | | |
|---|---|---|---|---|---|
| | | 2 | 4 | 6 | 8 |
| CONTROL | 20 | 5 | 45 | 75 | 80 |
| AgSD (Alone)* | | | | | |
| 30 mM | 20 | 25 | 65 | 75 | 75 |
| 15 mM | 20 | 10 | 50 | 80 | 100 |
| PPR (Alone)** | | | | | |
| 30 mM | 20 | 0 | 0 | 0 | 15 |
| 20 mM | 20 | 0 | 0 | 40 | 50 |
| 15 mM | 20 | 0 | 25 | 40 | 65 |
| AgSD + PPR (Combination) | | | | | |
| 30 mM AgSD + 30 mM PPR | 20 | 0 | 0 | 0 | 0 |
| 30 mM AgSD + 20 mM PPR | 20 | 0 | 20 | 20 | 20 |
| 30 mM AgSD + 15 mM PPR | 20 | 0 | 20 | 25 | 25 |
| 15 mM AgSD + 30 mM PPR | 20 | 0 | 0 | 0 | 10 |
| 15 mM AgSD + 20 mM PPR | 20 | 0 | 0 | 0 | 10 |

Drug concentration is mM per Kg of ointment used in therapy.
*AgSD — Silver Sulfadiazine
**PPR — Sodium Piperacillin
This table is the summary of three or four experiments.

TABLE VII
Topical Therapy of Burned Mice Infected with *Pseudomonas aeruginosa* (94-2) - Resistant

| GROUP | No. of Mice | % Mortality - Days Post Burn | | | |
|---|---|---|---|---|---|
| | | 2 | 4 | 6 | 8 |
| CONTROL | 20 | 70 | 70 | 100 | 100 |
| 30 mM AgSD* | 20 | 20 | 90 | 100 | 100 |
| 30 mM PPR** | 20 | 0 | 20 | 80 | 80 |
| 30 mM PPR + 30 mM AgSD | 20 | 0 | 0 | 25 | 35 |

Drug concentration is mM per Kg of ointment used in therapy.
*AgSD — Silver Sulfadiazine
**PPR — Sodium Piperacillin

TABLE VIII
Topical Therapy of Burned Rats Infected with *Pseudomonas aeruginosa* (MNG-4)

| GROUPS | No. of Rats | % Mortality - Days Post Burn | | | |
|---|---|---|---|---|---|
| | | 3 | 6 | 9 | 12 |
| CONTROL | 6 | 33 | 66 | 100 | 100 |
| 30 mM AgSD* | 6 | 0 | 66 | 100 | 100 |
| 30 mM PPR** | 6 | 0 | 0 | 0 | 0 |
| 30 mM PPR + 30 mM AgSD | 6 | 0 | 0 | 0 | 0 |

*AgSD — Silver Sulfadiazine
**PPR — Sodium Piperacillin

TABLE IX
Body Weight of Burned and Infected Rats Treated with Different Topical Agents

| GROUPS | DAYS POST BURN | | | | | | |
|---|---|---|---|---|---|---|---|
| | 1 | 2 | 4 | 6 | 8 | 10 | 12 |
| CONTROL | 190 | 160 | died | | | | |
| 30 mM AgSD* | 199 | 167 | died | | | | |
| 30 mM AgSD + 30 mM PPR** | 199 | 196 | 192 | 198 | 199 | 201 | 201 |

*AgSD — Silver Sulfadiazine
**PPR — Sodium Piperacillin
Burned rats were infected with *Pseudomonas aeruginosa* (MNG-4) from Table VIII. The body weight, in grams, was recorded on alternate days. Figures are the average of the groups listed in Table VIII.

What is claimed is:

1. An antibacterial composition useful in burn therapy comprising silver sulfadiazine, sodium piperacillin and a physiologically acceptable carrier, said composition containing a total of from about 35 millimoles to about 60 millimoles of silver sulfadiazine and sodium piperacillin per kilogram of the composition in a millimole ratio of silver sulfadiazine to sodium piperacillin of from about 2:1 to about 1:2.

2. An antibacterial composition defined by claim 1 containing about 30 millimoles of silver sulfadiazine per kilogram of the composition and about 30 millimoles of sodium piperacillin per kilogram of the composition.

3. An antibacterial composition defined by claim 1 containing about 30 millimoles of silver sulfadiazine per kilogram of the composition and about 20 millimoles of sodium piperacillin per kilogram of the composition.

4. An antibacterial composition defined by claim 1 containing about 30 millimoles of silver sulfadiazine per kilogram of the composition and about 15 millimoles of sodium piperacillin per kilogram of the composition.

5. An antibacterial composition defined by claim 1 containing about 15 millimoles of silver sulfadiazine per kilogram of the composition and about 30 millimoles of sodium piperacillin per kilogram of the composition.

6. An antibacterial composition defined by claim 1 containing about 15 millimoles of silver sulfadiazine per kilogram of the composition and about 20 millimoles of sodium piperacillin per kilogram of the composition.

7. A method of treating burns in animal or man which comprises topically applying an effective antibacterial amount of the composition of claim 1 to the affected surface.

* * * * *